(12) United States Patent
Perez-Cruet et al.

(10) Patent No.: US 9,775,653 B2
(45) Date of Patent: Oct. 3, 2017

(54) METHOD FOR SURGICALLY ATTACHING A VERTEBRAL LAMINAR RECONSTRUCTIVE PLATE

(75) Inventors: Miguelangelo J. Perez-Cruet, Bloomfield, MI (US); John R. Pepper, Cheshire, CT (US)

(73) Assignee: MI4SPINE, LLC, Bloomfield Hills, MI (US)

(*) Notice: Subject to any disclaimer, the term of this patent is extended or adjusted under 35 U.S.C. 154(b) by 915 days.

(21) Appl. No.: 13/226,337

(22) Filed: Sep. 6, 2011

(65) Prior Publication Data

US 2012/0071931 A1    Mar. 22, 2012

Related U.S. Application Data

(60) Provisional application No. 61/383,584, filed on Sep. 16, 2010.

(51) Int. Cl.
*A61B 17/88*     (2006.01)
*A61B 17/70*     (2006.01)

(52) U.S. Cl.
CPC .................. *A61B 17/7071* (2013.01)

(58) Field of Classification Search
CPC ............... A61B 17/7071; A61B 17/70
USPC ................... 606/70, 71, 246–299
See application file for complete search history.

(56) References Cited

U.S. PATENT DOCUMENTS

| | | | |
|---|---|---|---|
| 2003/0125738 A1* | 7/2003 | Khanna | 606/61 |
| 2004/0030388 A1* | 2/2004 | Null et al. | 623/17.11 |
| 2005/0043799 A1* | 2/2005 | Reiley | 623/17.11 |
| 2010/0161056 A1* | 6/2010 | Voellmicke et al. | 623/17.11 |

* cited by examiner

*Primary Examiner* — Si Ming Ku
(74) *Attorney, Agent, or Firm* — John A. Miller; Miller IP Group, PLC

(57) ABSTRACT

A method for attaching a laminar plate to a vertebra during spinal surgery, especially minimally invasive spinal surgery, to reconstruct the lamina of the vertebra after it has been removed during the surgery and prevent bone re-growth material from entering the spinal canal. The laminar plate can be coupled to, or proximate to, and between a facet and the spinous process by screwing the plate to the bone.

18 Claims, 7 Drawing Sheets

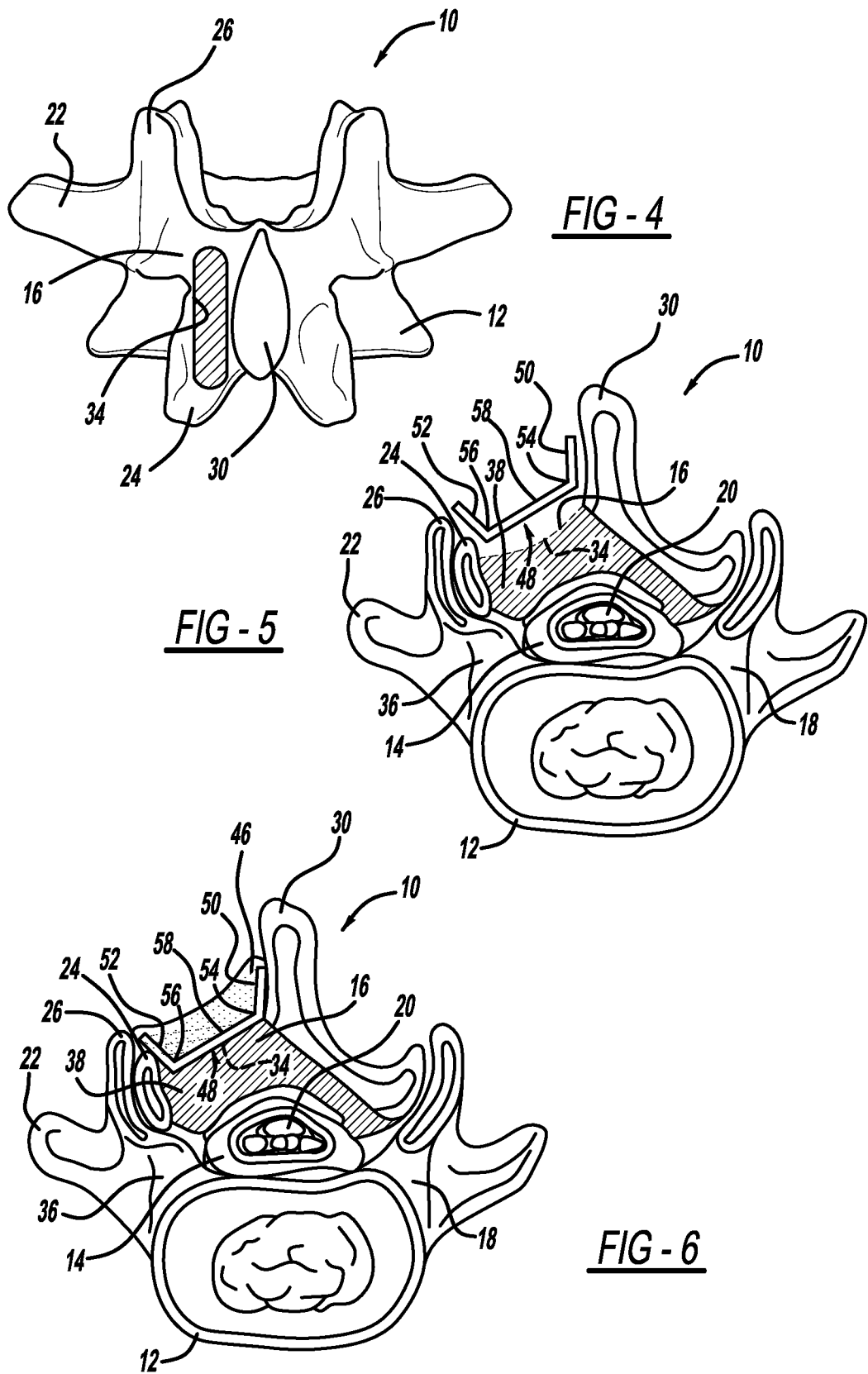

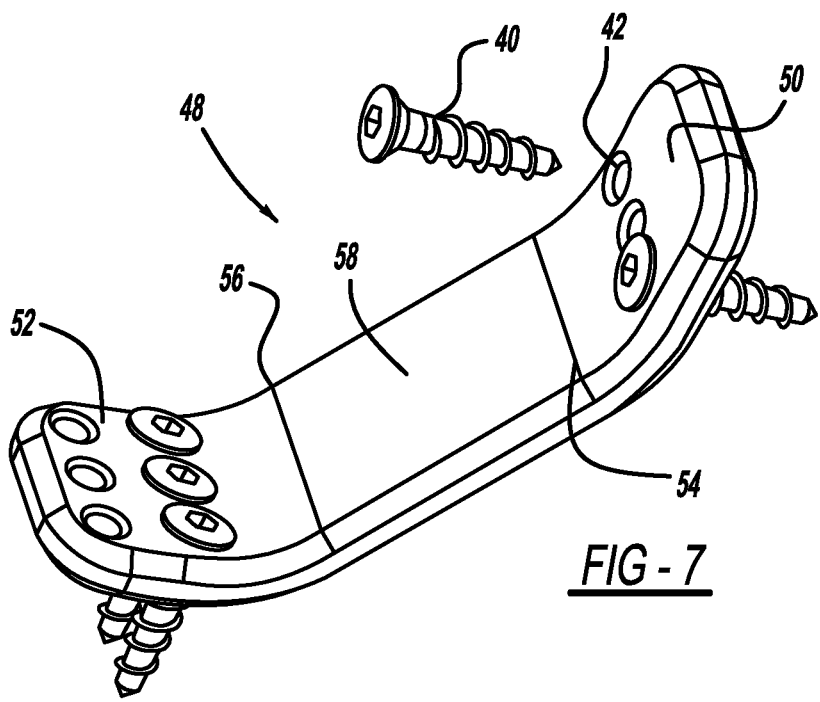
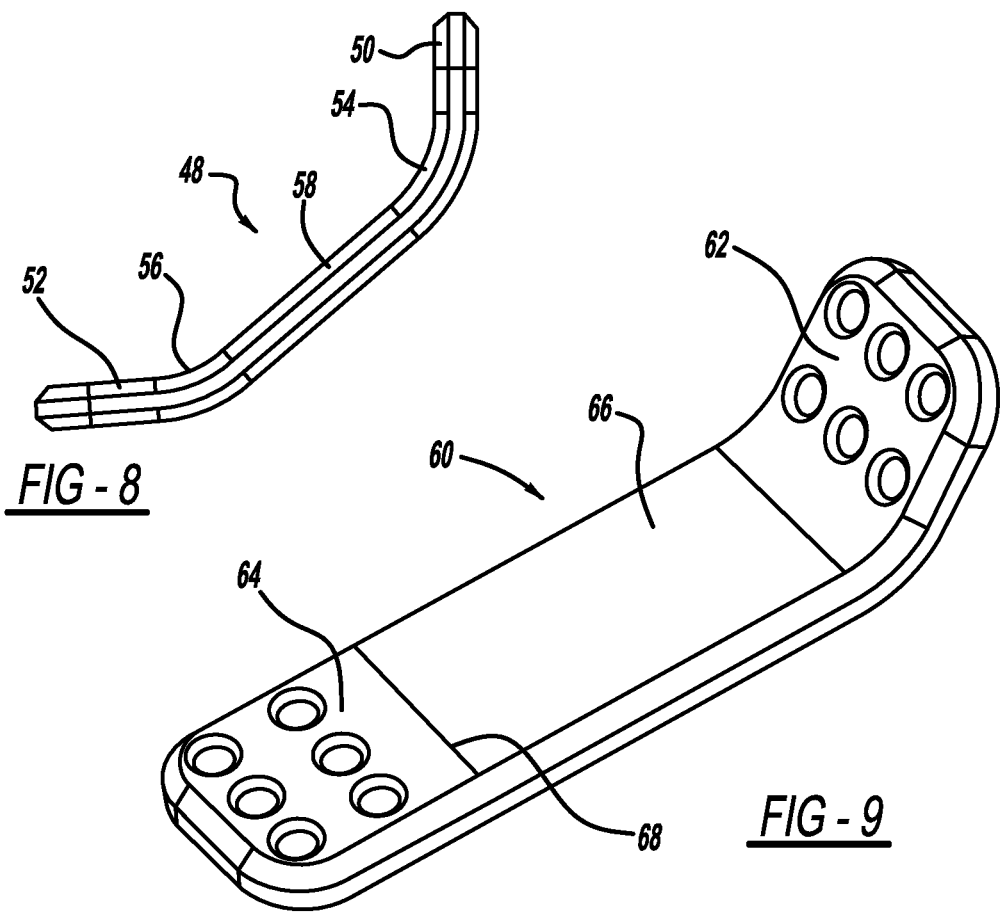

METHOD FOR SURGICALLY ATTACHING A VERTEBRAL LAMINAR RECONSTRUCTIVE PLATE

CROSS REFERENCE TO RELATED APPLICATIONS

This application claims the benefit of the priority date of U.S. Provisional Patent Application No. 61/383,584, titled Minimally Invasive Vertebral Laminar Reconstructive Plate, filed Sep. 16, 2010.

BACKGROUND OF THE INVENTION

Field of the Invention

Minimally invasive surgery (MIS) for the spine has established itself on the cutting edge for patients seeking surgical treatment of common spinal disorders with decreased perioperative pain, reduced blood loss, shorter hospitalization, easier and shorter recovery, and, most importantly, equivalent long-term efficacy as compared to open surgical procedures.

MIS for the spine began with simple decompression procedures for lumbar disc herniations. Next, surgeons used MIS surgical techniques to perform decompressions for lumbar stenosis and cervical discectomies and decompressions. Subsequently, surgeons implanted spinal instrumentation using minimally invasive techniques. Now, a surgeon can accomplish the vast majority of commonly performed spinal surgeries using minimally invasive techniques.

Several MIS spinal surgeries approach the spine through the lamina of the vertebra by drilling, cutting away or totally removing the lamina bone. Surgeries such as cervical laminectomy, lumbar discectomy and lumbar laminectomy are examples where the procedure can be performed through the lamina, which results in a compromised lamina having a hole or gap. One common procedure that can be performed with MIS for the spine is lumbar laminectomy for stenosis.

FIG. 1 is a top view and FIG. 2 is a posterior view of a vertebra 10 including a vertebral body 12, a spinal canal 14 through which the spinal cord and nerves 20 travel, a spinous process 30, pedicles 18 on both sides of the spinous process 30, a neural foramina 36 adjacent to the pedicles 18 through which nerves that leave the canal 14 travel, a superior articular facet 26 on both sides of the spinous process 30 that are part of a facet complex joint including the superior facet 26 of the vertebra 10 and an inferior articular facet of an adjacent vertebra (not shown), an inferior articular facet 24 on both sides of the spinous process 30 that are part of a facet complex joint including the inferior facet 24 of the vertebra 10 and a superior articular facet of an adjacent vertebra (not shown), a transverse process 22 on both sides of the spinous process 30, a lamina 16 between the superior facet 26 and the spinous process 30 on both sides of the vertebra 10, and a ligamentum flavum 38 beneath the lamina 16.

The vertebra 10 has stenosis, where the lamina 16, facet complex and the ligamentum flavum 38 have enlarged and grown into the spinal canal 14 causing narrowing of the spinal canal 14 so that it is more triangular shaped instead of oval shaped, resulting in compression of the nerves 20. The bone growth of the lamina 16, facet complex and the ligamentum flavum 38 can occur because of various reasons including degradation of the facet joint and/or instability, where the facet joint contacts the superior articular facet 26 and the inferior articular facet from the next lower vertebra.

The patient can experience pain and/or numbness from this narrowing of the spinal canal 14 because it contacts and pinches nerves.

In one surgical procedure to perform lumbar laminectomy for stenosis with MIS techniques, the surgeon makes an incision 1.5 cm lateral to the midline. The incision is placed directly over the disc with the stenosis. An 18 gauge spinal needle and lateral fluoroscopy identify the location of the stenosis. The surgeon cuts the fascia with a Bovey cautery, which helps to facilitate passage of a K-wire and subsequent muscle dilators. The surgeon docks the K-wire on the laminar facet junction followed by an initial muscle dilator, and then removes the K-wire. The surgeon then slips increasingly larger muscle dilators over the preceding muscle dilators. Finally, the surgeon places a tubular retractor or an expandable MIS retractor over the stack of dilators. Access to the vertebra 10 is achieved when the surgeon removes all of the dilators leaving the tubular retractor. At this point the surgeon can bring a microscope into the operative field. Palpation of the facet complex lateral can be preformed and the "drop off" point between the facet and the laminar-facet junction can be palpated with the Bovey tip. The tubular retractor should be positioned to rest on the facet, but allow the ipsilateral lamina to be easy viewed. If needed, an antero-posterior fluoroscopic view can be preformed to confirm the retractor location.

The surgeon manipulates a drill tip through the tubular retractor to remove a portion of the lamina 16, leaving behind a hole or open area 34 in the lamina 16 defined by the removed lamina bone. A skilled surgeon can decompress both sides of the vertebra 10 by choosing an angular entry to have the drill access and undercut the contralateral lamina. Once adequate decompression has been achieved, the tubular retractor is removed allowing the paraspinal muscles to return to their normal anatomical location. The surgeon sutures the subcutaneous tissues and closes the skin with an adhesive.

FIG. 3 is a cross-sectional view and FIG. 4 is a posterior view of the vertebra 10 showing the open area 34 resulting from the removed lamina bone including both the ipsilateral lamina bone and the contralateral lamina bone that has been removed by undercutting the spinous process 30 and contralateral lamina with a drill. Note that the spinal canal 14 is no longer narrowed, or triangular shaped, but has been restored to the more appropriate oval shape.

Although this procedure has left the spinous process 30 in place, and has restored the spinal canal 14, it still leaves the vertebra 10 structurally compromised, but where the spinous process 30 has been preserved including the muscle attachments to the spinous process 30. Particularly, the minimally invasive surgical technique for lumbar laminectomy for stenosis, and other surgeries, leaves the patient with a missing or damaged lamina 16. Also, in the case of laminectomy procedures, the remaining contralateral lamina may have been compromised by the undercutting of the lamina 16 to enlarge the spinal canal to relieve the pressure on the contralateral lamina side.

Bone graft material can be placed in the open area 34 where the lamina bone has been removed. However, the bone graft material can grow into the spinal canal 14. What is needed is a technique to replace the lost lamina bone that occurs during these types of surgical procedures while minimizing the risk that bone growth will encroach on the spinal canal.

SUMMARY OF THE INVENTION

In accordance with the teachings of the present invention, a method for attaching a laminar plate to a vertebra during spinal surgery, especially minimally invasive spinal surgery, is disclosed to reconstruct the lamina of the vertebra after it has been removed during the surgery and prevent bone re-growth material from entering the spinal canal. The laminar plate can be coupled to, or proximate to, and between a facet and the spinous process of the vertebra by screwing the plate to the bone.

Additional features of the present invention will become apparent from the following description and appended claims, taken in conjunction with the accompanying drawings.

BRIEF DESCRIPTION OF THE DRAWINGS

FIG. 4 is a posterior view of the vertebra shown in FIG. 1 with the portion of the lamina removed;
FIG. 5 is a cross-sectional view of the vertebra shown in FIG. 3 and including a laminar plate;
FIG. 6 is a cross-sectional view of the vertebra shown in FIG. 3 and including the laminar plate with bone graft material deposited over the plate;
FIG. 7 is a perspective view of the laminar plate shown separate from the vertebra;
FIG. 8 is a side view of the laminar plate shown in FIG. 7;
FIG. 9 is a perspective view of a laminar plate with a single angled end.

DETAILED DESCRIPTION OF THE EMBODIMENTS

The following description of the embodiments of the invention directed to a laminar plate for supporting a vertebra as a result of lamina bone that was removed from the vertebra during spinal surgery is merely exemplary in nature and does not limit the invention, its application or uses.

Figure 1:
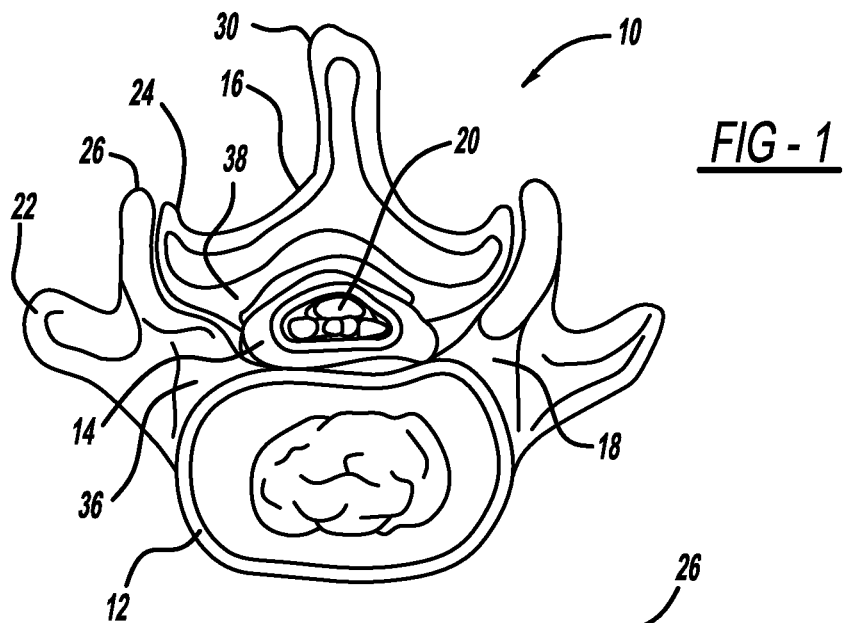
FIG. 1 is a top view of a vertebra with stenosis.
Figure 2:
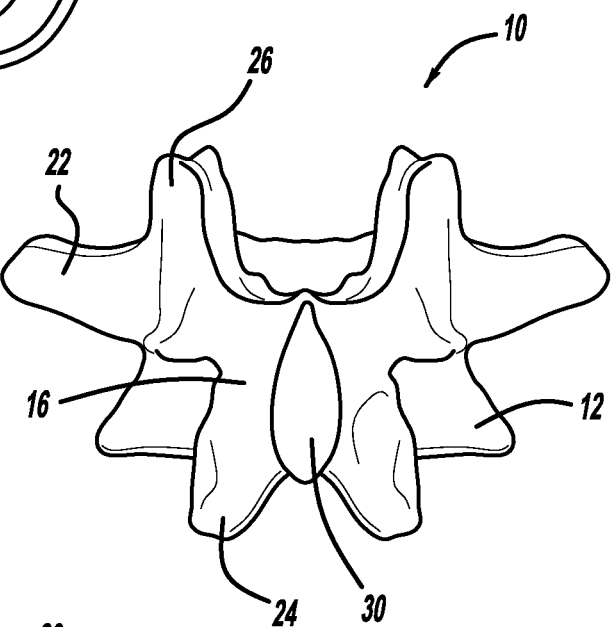
FIG. 2 is a posterior view of the vertebra shown in FIG. 1.
Figure 3:
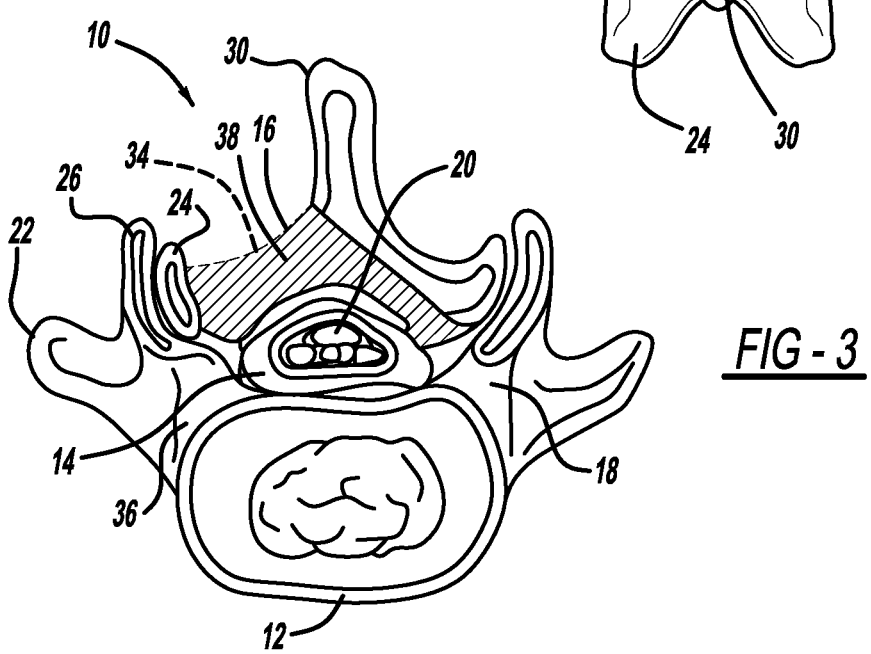
FIG. 3 is a cross-sectional view of the vertebra shown in FIG. 1 with a portion of the lamina removed.

FIG. 5 is a cross-sectional view of the vertebra 10 as shown in FIG. 3 with a laminar plate 48 positioned across the open area 34 from the removed lamina bone. As will be discussed in detail below, the laminar plate 48 provides a brace for the vertebra 10 that is desirable to support the vertebra because of the lamina bone that was removed during the particular surgical procedure discussed above.

Also, the plate 48 provides a platform on which bone growth material can be placed to provide further support for the removed lamina bone. FIG. 6 is the cross-sectional view of the vertebra 10 with the laminar plate 48 positioned across the open area 34 and showing a layer of bone growth material 46 deposited on the plate 48. The bone growth material 46 provides a fusion material that restores the integrity of the removed lamina bone. The plate 48 prevents the bone growth material 46 from falling into the spinal canal 14 and/or the foramina 36 and compressing the nerves. The bone growth material can be any material suitable for the purposes discussed herein, and can include local bone material that has been drilled and collected from the vertebra 10 when the lamina bone was removed.

FIG. 7 is a perspective view and FIG. 8 is a side view of the laminar plate 48 removed from the vertebra 10. The laminar plate 48 is primarily a flat elongated plate member having a bend at each end. Particularly, the plate 48 includes a first end 50 connected to a center plate portion 58 at a first bend 54 and a second end 52 connected to an opposite end of the center plate portion 58 at a second bend 56. The angle of the first bend 54 is a positive angle measured from a backside of the plate portion 58 that directs the first end 50 away from a backside of the plate portion 58 to allow the first end 50 to be acceptably coupled to the spinous process 30. The angle of the second bend 56 is a positive angle measured from the backside of the plate portion 58 that directs the second end 52 away from the backside of the plate portion 58 to allow the second end 52 to be acceptably coupled to the facet 24.

The laminar plate 48 can be mounted to bony portions of the vertebra 10 at any suitable location and by any suitable technique. In this non-limiting embodiment, the first end 50 includes a single row of three holes 42 that accept screws 40, which are threaded into the spinous process 30 to hold the first end 50 of the plate 48 in place, and the second end 52 includes two rows of three holes 42 through which the screws 40 are inserted to mount the second end 52 of the plate 48 to the facet 24. The second end 52 can attach to the bone of the facet 24 in any suitable manner. For example, if the facet joint is operating properly, the second end 52 can attach just to the facet 24 or can attach to both the facet 24 and the inferior articular facet of the adjacent vertebra if it is desired to immobilize the facet joint. This is especially true if degradation in the facet joint may cause bone growth that could lead to the narrowing of the spinal canal 14.

The screws 40 can be any screw suitable for the purposes discussed herein, such as maxial-cranial screws (about 1.5 mm major diameter), which are commonly used in facial surgery. Although the embodiments discussed herein employ screws for attaching the laminar plate 48 to bone, other methods of attachment may be possible, such as pins, a press fit, bone cement, locking screws, etc.

Further, the present invention contemplates any suitable configuration, orientation, length, angle, etc. for the laminar plate 48 that allows it to be securely mounted to the vertebra 10 depending on the particular circumstances of the surgical procedure, the condition of the vertebra, the amount of lamina bone removed, etc. There are various surfaces that may be available to attach the first end 50 and the second end 52 of the laminar plate 48 to the bone of the vertebra 10.

The laminar plate 48 may include small structures that will enable bone growth into surfaces to become part of a solid fusion mass. The surgeon can cut into the bone to make a slot or notch for the brace to fit into or attach thereto. The plate surfaces can be impregnated with bone growth enhancing compounds where it is desirable to have bone growth occur. The plate surfaces can be smooth where it is not desirable to have solid bone integration. The plate surface can also be impregnated with compounds that deter bone growth in areas where bone should be absent.

The laminar plate 48 can be installed with bone re-growth promoters. There are various sources for bone growth material including bone growth material harvested from drilling of the patient's lamina, bone growth material drilled from some other part of the patient, bone material harvested from a cadaver, bone growth material from any other commercially available material that facilitates bone growth, etc. Also, the bone growth material can have bone growth enhancing compounds in it.

The laminar plate 48 can be made of any material suitable for the purposes discussed herein, including metal, plastic, dissolvable materials, biologics, tissue graft or any other material found to be suitable for the application. Any material that can provide a rigidity while the bone re-grows and fuses together or permanent rigidity may be suitable.

The laminar plate 48 can attach to the original bone surfaces or can attach to newly exposed bone surfaces. In addition, the plate 48 can be fastened out of a metal material that can be plastic deformed by a surgeon's hands. This enables the angle of the attach surfaces to be adjusted based upon the situation the surgeon is faced with after the spinal surgery has been complete and are looking to restore the lamina. Alternatively, the plate 48 can be plastic deformable by a hand-held device, such as a pair of pliers.

FIG. 9 is a perspective view of a laminar plate 60 of the type discussed herein, similar to the laminar plate 48, that can be positioned across the open area 34. The plate 60 includes a first end 62 and a second end 64 connected by a center plate portion 66. The first end 62 is angled relative to the connecting portion 66 and the second end 64 is not angled relative to the connecting portion 66, as shown.

Figure 10:
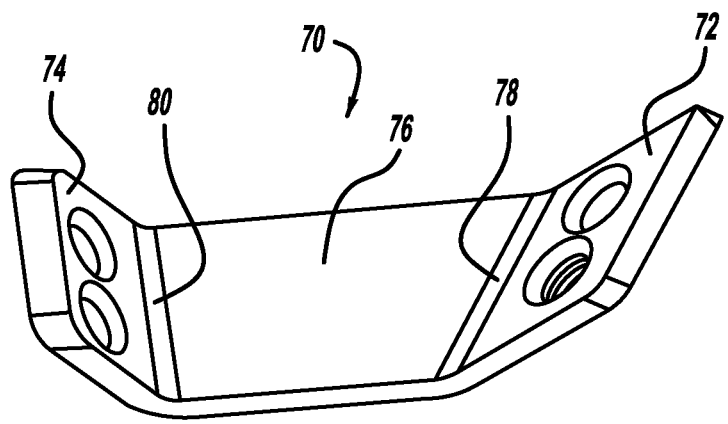
FIG. 10 is a perspective view of a laminar plate with compound end angles.

FIG. 10 is a perspective view of a laminar plate 70 of the type discussed herein that can be positioned across the open area 34. The plate 70 includes a first end 72 and a second end 74 connected by a center plate portion 76, where the angle between the ends 72 and 74 and the connecting portion 76 are complex angles, as shown. In this embodiment, screws can be placed through the facet joint to immobilize the joint, which helps lock bone surfaces in position while the bone fusion is occurring. In addition, by locking the facet joint, the surgeon can avoid aggravation at the joint that could lead to undesirable bone growth into the foramen canal. To immobilize the facet joint, the screw is driven through the inferior articular facet and the superior articular facet to immobilize in the joint. In this embodiment, the first end 72 and the second end 74 each include only two screw holes.

Figure 11:
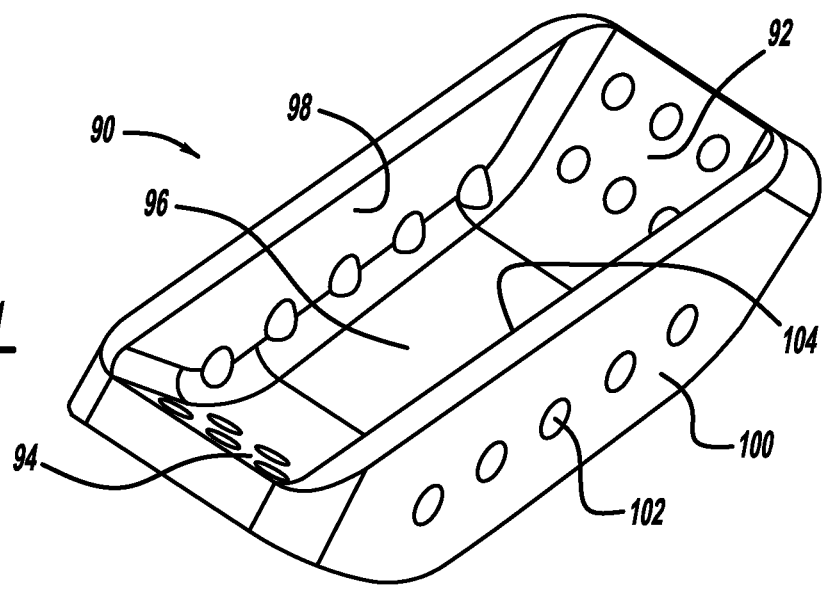
FIG. 11 is a perspective view of a laminar plate with a bone trough.

FIG. 11 is a perspective view of a laminar plate 90 of the type discussed herein, similar to the laminar plate 48, that can be positioned across the open area 34. The plate 90 includes a first end 92 and a second end 94 connected by a center plate portion 96. The plate 90 also includes opposing side walls 98 and 100 provided relative to the angle of the ends 92 and 94 so that a trough 104 is formed that is able to accept and hold significant bone growth material. Openings 102 in the sidewalls 98 and 100 allow bone growth to extend therethrough to further facilitate mounting of the plate 90 to the vertebra 10.

Figure 12:
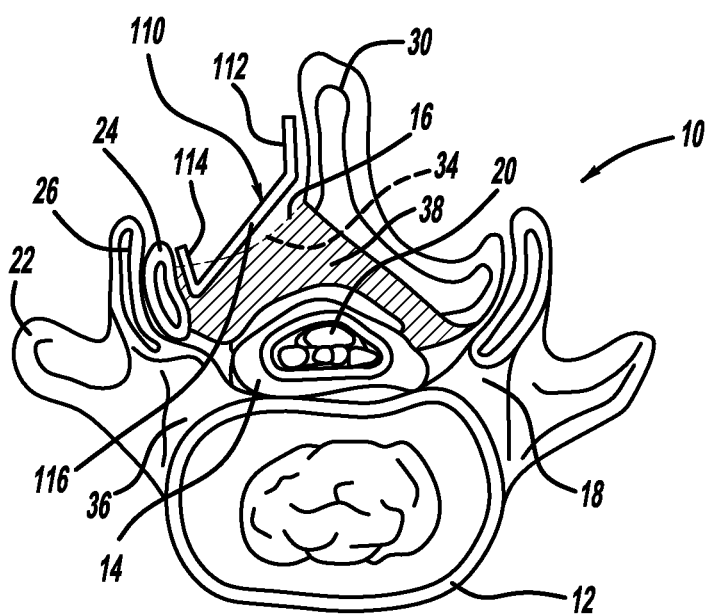
FIG. 12 is a cross-sectional view of the vertebra as shown in FIG. 3 and including another laminar plate.

FIG. 12 is a cross-sectional view of the vertebra 10 showing a laminar plate 110 of the type discussed herein positioned across the open area 34. The plate 110 includes a first end 112 and a second end 114 connected by a center plate portion 116, where the ends 112 and 114 have a special angle and configuration for the open area 34. The bend between the end 112 and the center plate portion 116 is less than 90° to enable the first end 112 to better attach to the spinous process 30 for some procedures. This allows coupling to the spinous process 30 that is a more solid surface than the newly exposed interior bone. One advantage for attaching to the drill-exposed facet bone is that it should be easier for the surgeon to access and drive a screw into the bone near the facet joint.

Figure 13:
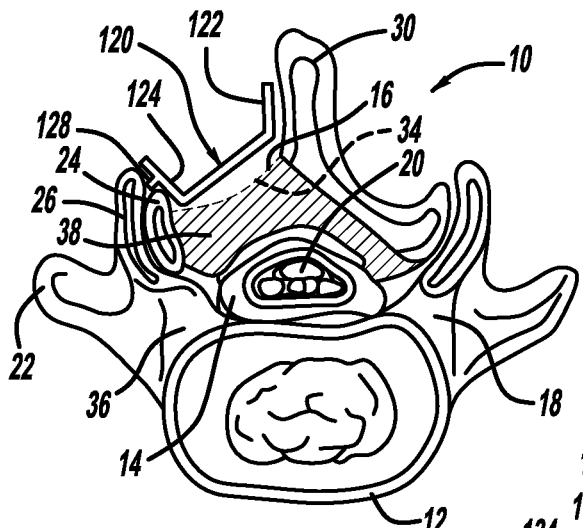
FIG. 13 is a cross-sectional view of the vertebra as shown in FIG. 3 and including another laminar plate.

FIG. 13 is a cross-sectional view of the vertebra 10 showing a laminar plate 120 of the type discussed herein positioned across the open area 34. The plate 120 includes a first end 122 and a second end 124 connected by a center plate portion 126, where the first and second ends 122 and 124 have a special angle for the open area 34. The second end 124 includes a nub 128 that facilitates coupling of the plate 120 to the facet joint.

Figure 14:
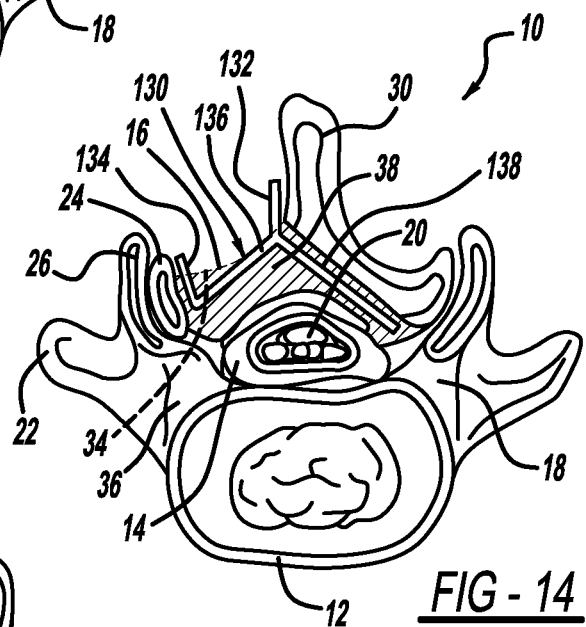
FIG. 14 is a cross-sectional view of the vertebra as shown in FIG. 3 and including another laminar plate.

FIG. 14 is a cross-sectional view of the vertebra 10 showing a laminar plate 130 of the type discussed herein positioned across the open area 34. The laminar plate 130 includes a first end 132 and a second end 134 connected by a center plate portion 136. An extended portion 138 extends from the plate portion 136 proximate the end 132 and is positioned within the open area 34, as shown. The extended portion 138 extends the length of the undercut exposed bone, and can attach or provide support to the contralateral lamina bone.

Figure 15:
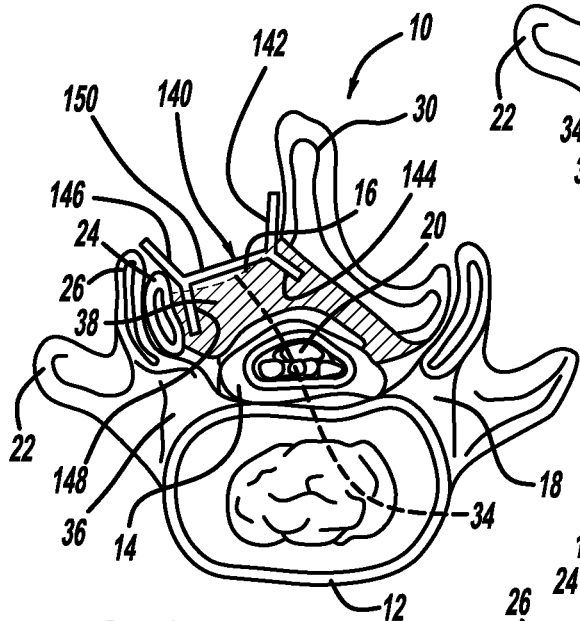
FIG. 15 is a cross-sectional view of the vertebra as shown in FIG. 3 and including another laminar plate.

FIG. 15 is a cross-sectional view of the vertebra 10 showing a laminar plate 140 of the type discussed herein positioned across the open area 34. The plate 140 includes opposing extensions 142 and 144 extending from one end of a center plate portion 150 and opposing extensions 146 and 148 extending from an opposite end of the connection portion 150 in a "dog-bone" type configuration, as shown. One advantage of the dog-bone configuration is that it is a simple structure that allows the plate 140 to be easily installed.

Figure 16:
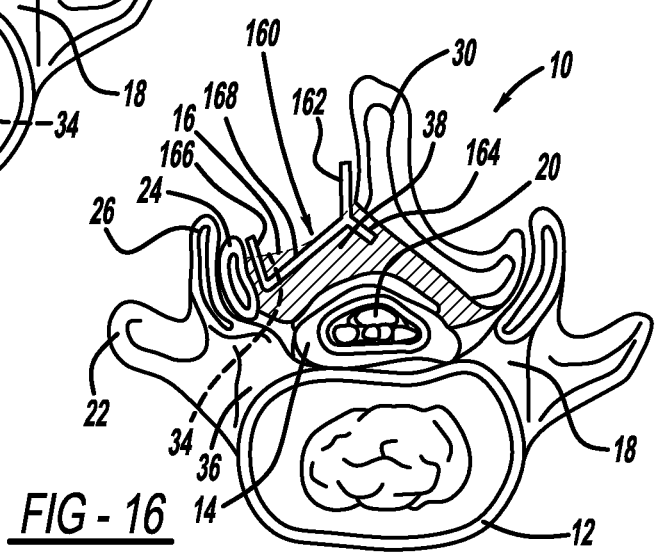
FIG. 16 is a cross-sectional view of the vertebra as shown in FIG. 3 and including another laminar plate.

FIG. 16 is a cross-sectional view of the vertebra 10 showing a laminar plate 160 of the type discussed herein positioned across the open area 134. The plate 160 includes a first end 162 and a second end 166 connected by a center plate portion 168. An extension 164 extends from the plate portion 168 opposite to the first end 162, as shown. The second end 166 is rotated to allow the second end 166 to attach to the exposed bone near the facet 24. The plate 160 is expected to make it easier for the surgeon to install the lamina plate 160 because during installation of the plate 160, the end 162 can cradle the point where the spinous process bone ends and the new drill-exposed bone begins. Also, the second end 166 is accessible to drive a screw into the bone near the facet joint or through the facet joint.

Figure 17:
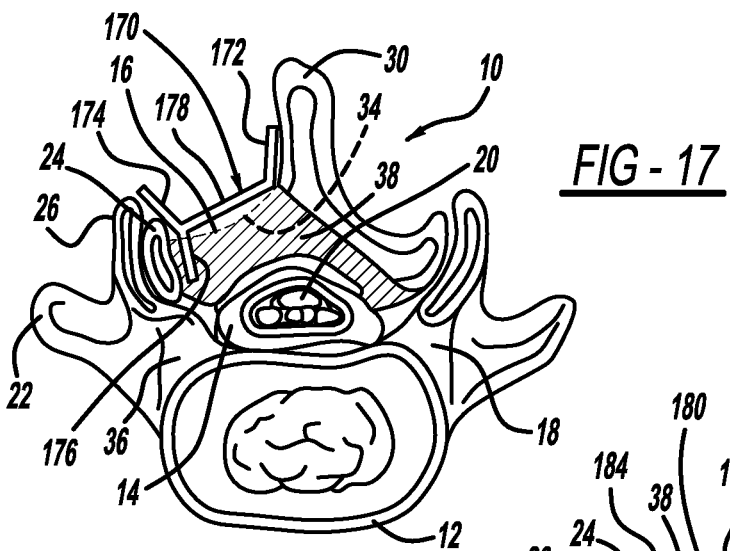
FIG. 17 is a cross-sectional view of the vertebra as shown in FIG. 3 and including another laminar plate.

FIG. 17 is a cross-sectional view of the vertebra 10 showing a laminar plate 170 of the type discussed herein positioned across the open area 34. The laminar plate 170 includes a first end 172 and a second end 174 connected by a center plate portion 178. An extension member 176 extends from the plate portion 178 opposite to the second end 174. The first end 172 can be rotated less than 90° from the plate portion 178 to allow the first end 172 to attach to the spinous process 30. The laminar plate 170 is expected to make it easier for the surgeon to install the plate 170 because during installation, the end 174 and the extension member 176 can cradle the facet joint, and the first end 172 can be rotated until it hits the spinous process 30. Then, the first end 172 will also be accessible to drive a screw into the spinous process 30.

Figure 18:
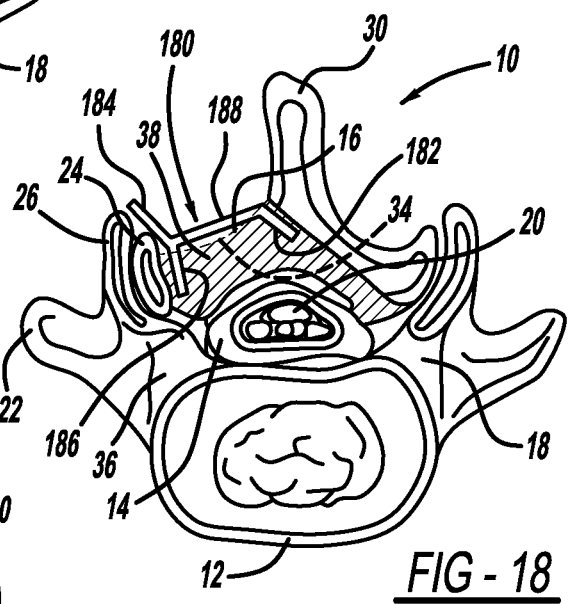
FIG. 18 is a cross-sectional view of the vertebra as shown in FIG. 3 and including another laminar plate.

FIG. 18 is a cross-sectional view of the vertebra 10 showing a laminar plate 180 of the type discussed herein positioned across the open area 34. The laminar plate 180 includes a first end 182 and a second end 184 connected by a center plate portion 188. An extension member 186 extends from an end of the plate portion 188 proximate to and opposite from the second end 184. The first end 182 can be rotated less than 90° from the plate portion 188 to allow the first end 182 to attach to the spinous process 30. The laminar plate 180 is expected to make it easier for the surgeon to install the plate 180 because during installation, the end 184 and the extension member 186 can cradle the facet joint, and the first end 182 can be rotated until it contacts the spinous process 30. Then, the first end 182 will also be accessible to drive a screw into the spinous process 30.

Figure 19:
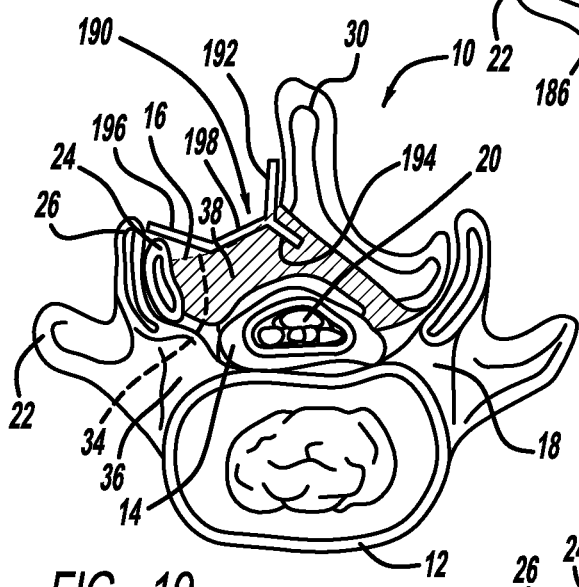
FIG. 19 is a cross-sectional view of the vertebra as shown in FIG. 3 and including another laminar plate.

FIG. 19 is a cross-sectional view of the vertebra 10 showing a laminar plate 190 of the type discussed herein positioned across the open area 34. The laminar plate 190 includes a first end 192 and a second end 196 connected by a center plate portion 198. An extension member 194 extends from an end of the plate portion 198 proximate to and opposite from the first end 192.

Figure 20:
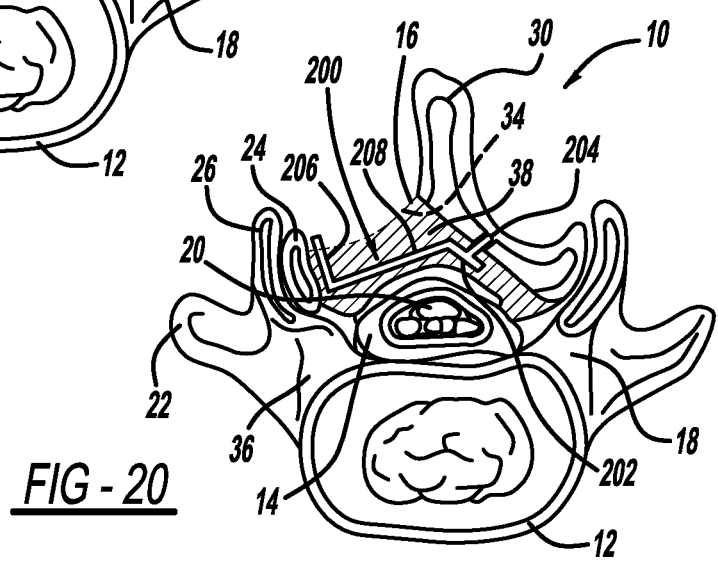
FIG. 20 is a cross-sectional view of the vertebra as shown in FIG. 3 and including another laminar plate.

FIG. 20 is a cross-sectional view of the vertebra 10 showing a laminar plate 200 of the type discussed herein positioned across the open area 34. The laminar plate 200 includes a first end 202 and a second end 206 connected by a center plate portion 208, where the first and second ends 202 and 206 extend from opposite sides of the plate portion 208. A peg 204 extends from the first end 202. One advantage of the plate 200 is that the end 202 can be easily located and orientated by inserting the peg 204 into a pre-drilled hole. Then, the surgeon rotates the laminar plate 200 until the second end 206 contacts the drill-exposed bone by the facet joint. The surgeon would have clear access to the second end 206 to be able to drive a screw into the bone proximate the facet joint.

Figure 21:
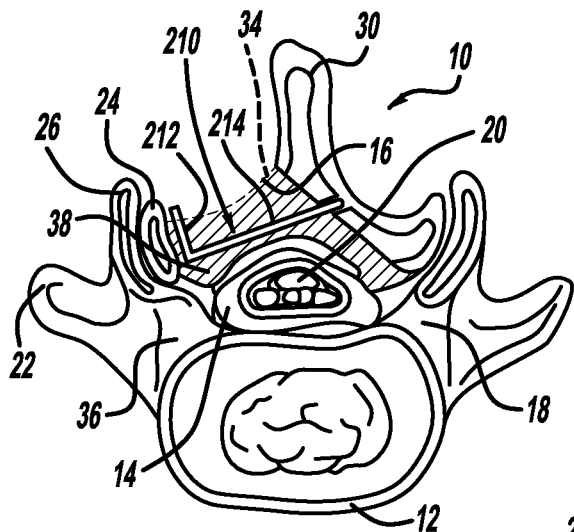
FIG. 21 is a cross-sectional view of the vertebra as shown in FIG. 3 and including another laminar plate.

FIG. 21 is a cross-sectional view of the vertebra 10 showing a laminar plate 210 of the type discussed herein positioned across the open area 34. The laminar plate 210 includes perpendicular portions 212 and 214 forming a simple L-shape.

Figure 22:
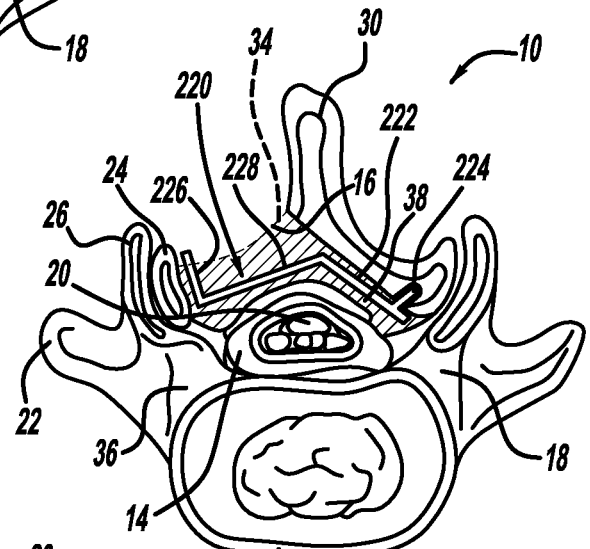
FIG. 22 is a cross-sectional view of the vertebra as shown in FIG. 3 and including another laminar plate.

FIG. 22 is a cross-sectional view of the vertebra 10 showing a laminar plate 220 of the type discussed herein positioned across the open area 34. The laminar plate 220 includes a first end 222 and a second end 226 connected by a center plate portion 228, where the ends 222 and 226 extend from opposite sides of the plate portion 228. The first end 222 includes a nub 224 extending therefrom. One advantage of the plate 220 is that the entire contralateral lamina bone is covered.

Figure 23:
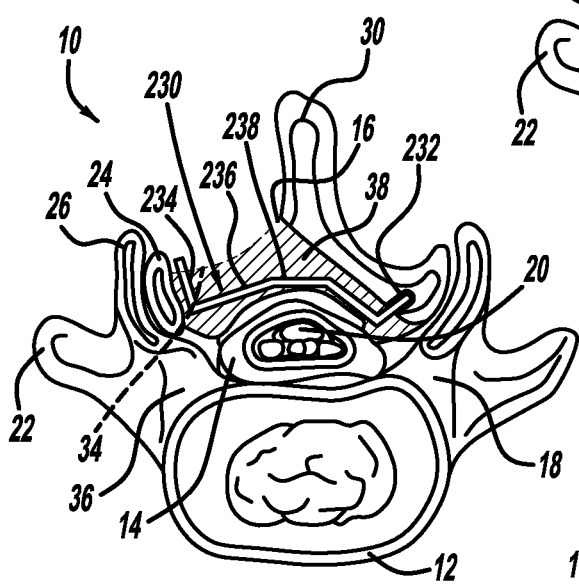
FIG. 23 is a cross-sectional view of the vertebra as shown in FIG. 3 and including another laminar plate.

FIG. 23 is a cross-sectional view of the vertebra 10 showing a laminar plate 230 of the type discussed herein positioned across the open area 34. The laminar plate 230 includes a first end 232 and a second end 234 connected by a center plate portion 236, where the plate portion 236 includes an angled portion 238. The laminar plate 230 provides a more proper reconstruction of the bone structure for the spinal canal 14 with the bend at the first end 232.

Figure 24:
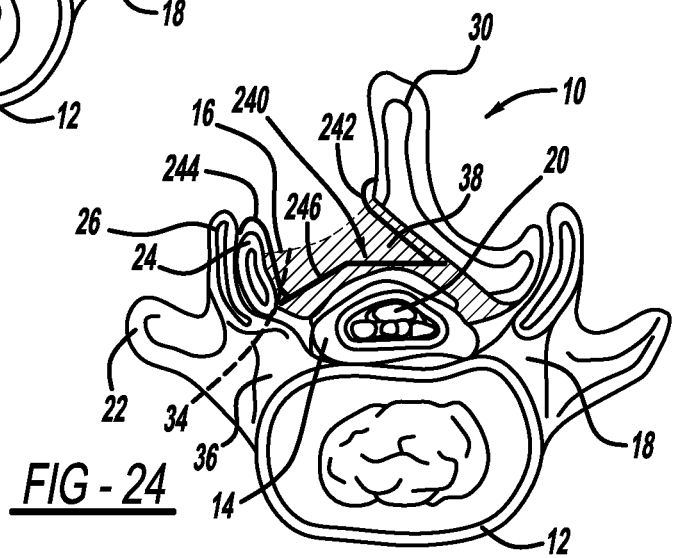
FIG. 24 is a cross-sectional view of the vertebra as shown in FIG. 3 and including another laminar plate.

FIG. 24 is a cross-sectional view of the vertebra 10 showing a laminar plate 240 of the type discussed herein positioned across the open area 34. The laminar plate 240 includes hooked ends 242 and 244 connected by a center plate portion 246, where the ends 242 and 244 pull up against the underside of the open area 34 in the lamina 16. In use, the laminar plate 240 is inserted through the open area 34 in the lamina 16 so that it is completely behind the lamina 16. Then, the hooks 242 and 244 are pulled up against the backside of the lamina opening. Once the tension has been established in the hooks 242 and 244, then the plate 240 should be held in place. The plate 240 can also be attached physically to the bone with screws or other mechanisms.

The surfaces of the laminar plates discussed herein could be formed to exactly match the inner contour of the vertebrae using 3-D scanning and fabricating technique, discussed in more detail below, to generate custom 3-D lamina plate. First a 3-D scan is made of the person's vertebrae. The scanned data is used to create a computer model of the vertebral bone. In the computer, the vertebrae model is used to create a surface representing the vertebra's lamina exterior surface. Then, a custom 3-D laminar plate is constructed in the computer that exactly matches the outer contour of the lamina exterior surface.

The custom 3-D plate has a custom match surface that is generated from the scanned 3-D surface of the patient's vertebrae bone. The custom match surface wraps around the sides of the lamina bone, extends from the facet 24 to the spinous process 30 and ends on the sides at the lamina wrapped edge on both the facet side and the spinous process side. The custom 3-D plate has a bone containment area that is the volume contained between the custom match surface and the bone growth constraint backstop extending from the facet side end to the spinous process side end. The containment area can hold bone re-growth material. The custom match surface can have holes to allow the bone re-growth material to be inserted into the bone containment area.

The custom 3-D lamina plate has a wrapping around the size of the original surface. The custom match surface does not have to wrap around the sides, it might just be a match to part of the lamina exterior bone surface. It is thought that by wrapping around the sides it will be easier to install the plate because the plate would automatically position itself. A thinner plate, or different sized plate, that only partially matches the outer surface of the original vertebrae could be used as well.

The plate construction is a rigid material that is also conducive to cutting. The plate has an outer surface that exactly matches the vertebra's outside surface.

Once the surgery is complete and the lamina hole or gap is defined, then the laminar plate can be trimmed to the appropriate size. It can be inserted down the minimally invasive access retractor and put in position. With the computer model of the bone the laminar plate can be constructed in the computer and built for installation using rapid prototyping techniques. Rapid prototyping techniques can construct a brace of metal or other suitable materials.

Another approach would be to use a computerized model of the vertebra after the lamina bone has been removed. Using this approach a plate can be constructed that will fit perfectly with the remaining bone structure. Also, the generated plate can be constructed so that it can fit through minimally invasive surgery opening.

The 3-D scan could be done during the surgical procedure and the laminar plate could be generated on-the-fly to match the newly drilled surfaces.

The foregoing discussion discloses and describes merely exemplary embodiments of the present invention. One skilled in the art will readily recognize from such discussion and from the accompanying drawings and claims that various changes, modifications and variations can be made therein without departing from the spirit and scope of the invention as defined in the following claims.

What is claimed is:

1. A method for supporting a vertebra, said method comprising:
    removing lamina bone from the vertebra during a lumbar laminectomy for stenosis surgical procedure to create an opening in the vertebra that exposes a spinal canal;
    providing a single piece continuous laminar plate including an elongated center plate portion, a first end portion coupled to a first end of the elongated plate portion and a second end portion coupled to a second end of the elongated plate portion;
    coupling the laminar plate to the vertebra to cover the opening created by the removed lamina bone, wherein the laminar plate is shaped and configured to be coupled to the vertebra so that the center plate portion is recessed in the opening and positioned at a location within the vertebra that is more inward toward the spinal canal than the first and second end portions such that the first and second end portions are angled from the center plate portion away from the spinal canal; and
    depositing bone growth material on the laminar plate to reinforce the vertebra.

2. The method of claim 1 wherein coupling the laminar plate to the vertebra includes attaching the first end portion of the laminar plate to a spinous process of the vertebra and attaching the second end portion of the laminar plate to a facet of the vertebra.

3. The method of claim 1 wherein coupling the laminar plate to the vertebra includes coupling the second end portion of the laminar plate to a superior articular facet of the vertebra.

4. The method of claim 3 wherein coupling the laminar plate to the vertebra includes coupling the second end portion of the laminar plate to both the superior articular facet of the vertebra and an inferior articular facet of another vertebra.

5. The method of claim 1 wherein coupling the laminar plate to the vertebra includes coupling the first end portion and the second end portion of the laminar plate to the vertebra using screws.

6. The method of claim 1 wherein the bone growth material is selected from the group consisting of local bone, synthetic bone graft material and biologics.

7. The method of claim 1 wherein the spinal surgery is a minimally invasive surgical technique.

8. The method of claim 1 wherein providing the laminar plate includes providing a laminar plate having a trough defined by the elongated center plate portion and opposing side walls.

9. The method of claim 8 wherein the opposing side walls include one or more fusion openings to facilitate bone fusion with bone of the vertebra.

10. The method of claim 1 wherein providing the laminar plate includes providing a laminar plate having one or more barriers that prevent bone from growing into undesirable areas of the vertebra.

11. The method of claim 1 wherein providing the laminar plate includes providing a laminar plate where the first end portion includes only a single first end piece angled other than 180° relative to the elongated center plate portion and the second end portion includes only a single second end piece angled other than 180° relative to the elongated center plate portion.

12. The method of claim 11 wherein providing the laminar plate includes providing a laminar plate where the first and second end pieces are angled in a same direction relative to the center plate portion.

13. The method of claim 11 wherein providing the laminar plate includes providing a laminar plate where the first and second end pieces are angled in opposite directions relative to the center plate portion.

14. The method of claim 1 wherein providing the laminar plate includes providing a laminar plate where the first end portion includes a first end piece angled other than 180° relative to the elongated center portion, the second end portion includes a second end piece angled other than 180° relative to the elongated center portion and one or both of the first or second end portion includes another end piece angled in an opposite direction from the first or second end piece.

15. A method for supporting a vertebra, said method comprising:
    removing lamina bone from the vertebra during a lumbar laminectomy for stenosis surgical procedure to create an opening in the vertebra that exposes a spinal canal;
    providing a single piece continuous laminar plate including an elongated center plate portion, a first end piece coupled to a first end of the elongated plate portion and a second end piece coupled to a second end of the elongated plate portion, wherein the first end piece is angled other than 180° relative to the elongated center plate portion and the second end piece is angled other than 180° relative to the elongated center plate portion;
    coupling the laminar plate to the vertebra to cover the opening created by the removed lamina bone, wherein coupling the laminar plate to the vertebra includes attaching the first end piece of the laminar plate to, or proximate to, a spinous process of the vertebra and attaching the second end piece of the laminar plate to, or proximate to, a facet of the vertebra, and wherein the laminar plate is shaped and configured to be attached to the vertebra so that the center plate portion is recessed in the opening and positioned at a location within the vertebra that is more inward toward the spinal canal than the first and second end pieces such that the first and second end pieces are angled from the center plate portion away from the spinal canal; and
    depositing bone growth material on the laminar plate to reinforce the vertebra.

16. The method of claim 15 wherein providing the laminar plate includes providing a laminar plate where the first and second end pieces are angled in a same direction relative to the center plate portion.

17. The method of claim 15 wherein coupling the laminar plate to the vertebra includes coupling the first end piece and the second end piece of the laminar plate to the vertebra using screws.

18. A method for supporting a vertebra, said method comprising:
    removing lamina bone from the vertebra during a lumbar laminectomy for stenosis surgical procedure to create an opening in the vertebra that exposes a spinal canal;
    providing a single piece continuous laminar plate including an elongated center plate portion, a first end portion coupled to a first end of the elongated plate portion and a second end portion coupled to a second end of the elongated plate portion;

coupling the laminar plate to the vertebra to cover the opening created by the removed lamina bone, wherein coupling the laminar plate to the vertebra includes coupling the first end portion and the second end portion of the laminar plate to the vertebra using screws, and wherein the laminar plate is shaped and configured to be attached to the vertebra so that the center plate portion is recessed in the opening and positioned at a location within the vertebra that is more inward toward the spinal canal than the first and second end portions such that the first and second end portions are angled from the center plate portion away from the spinal canal; and depositing bone growth material on the laminar plate to reinforce the vertebra on a surface of the plate opposite from the spinal canal.

* * * * *